United States Patent
Xie et al.

(10) Patent No.: US 12,146,183 B2
(45) Date of Patent: Nov. 19, 2024

(54) COMPOUND AND A METHOD FOR IDENTIFYING A PROTEIN USING SAID COMPOUND

(71) Applicant: CITY UNIVERSITY OF HONG KONG, Kowloon (HK)

(72) Inventors: Yusheng Xie, Kowloon (HK); Rui Wang, Kowloon (HK); Liang Zhang, Kowloon (HK); Hongyan Sun, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 233 days.

(21) Appl. No.: 17/350,934

(22) Filed: Jun. 17, 2021

(65) Prior Publication Data

US 2021/0395795 A1  Dec. 23, 2021

Related U.S. Application Data (60) Provisional application No. 63/040,060, filed on Jun. 17, 2020.

(51) Int. Cl.
| | | |
|---|---|---|
| *C12Q 1/32* | (2006.01) | |
| *C07D 413/12* | (2006.01) | |
| *C07K 7/06* | (2006.01) | |
| *C09K 11/06* | (2006.01) | |
| *C12N 9/02* | (2006.01) | |

(52) U.S. Cl.
CPC .............. *C12Q 1/32* (2013.01); *C07D 413/12* (2013.01); *C07K 7/06* (2013.01); *C09K 11/06* (2013.01); *C12N 9/0008* (2013.01); *G01N 2333/90203* (2013.01)

(58) Field of Classification Search
CPC .......... C12Q 1/32; C07D 413/12; C07K 7/06; C09K 11/06; C12N 9/0008; G01N 2333/90203
See application file for complete search history.

(56) References Cited

PUBLICATIONS

Chen, Yingche, Kelvin Tsao, and Jeffrey W. Keillor. "Fluorogenic protein labelling: a review of photophysical quench mechanisms and principles of fluorogen design." Canadian Journal of Chemistry 93.4 (2015): 389-398. (Year: 2015).*
Thermo Fisher Scientific, Photoreactive Crosslinker Chemistry; https://www.thermofisher.com/us/en/home/life-science/protein-biology/protein-biology-learning-center/protein-biology-resource-library/pierce-protein-methods/; accessed Feb. 21, 2023 (Year: 2022).*
Mackinnon AL, Taunton J. Target Identification by Diazirine Photo-Cross-linking and Click Chemistry. Curr Protoc Chem Biol. 2009 [Manuscript submitted for publication]. Dec;1:55-73. doi: 10.1002/9780470559277.ch090167. PMID: 23667793; PMCID: PMC3647699. (Year: 2009).*
Rowland EA, Snowden CK, Cristea IM. Protein lipoylation: an evolutionarily conserved metabolic regulator of health and disease. Curr Opin Chem Biol. Feb. 2018;42:76-85. doi: 10.1016/j.cbpa.2017.11.003. Epub Nov. 21, 2017. PMID: 29169048; PMCID: PMC5965299. (Year: 2018).*
Rowland, Elizabeth A, Caroline K Snowden, and Ileana M Cristea. "Protein Lipoylation: An Evolutionarily Conserved Metabolic Regulator of Health and Disease." Current opinion in chemical biology 42 (2018): 76-85. [Manuscript submitted for publication]. Web. (Year: 2018).*
Xie, Yusheng et al. "Chemical Probes Reveal Sirt2's New Function as a Robust 'Eraser' of Lysine Lipoylation." Journal of the American Chemical Society 141.46 (2019): 18428-18436. Web. (Year: 2019).*

* cited by examiner

*Primary Examiner* — Louise W Humphrey
*Assistant Examiner* — John Paul Selwanes
(74) *Attorney, Agent, or Firm* — Conley Rose, P.C.; Michael W. Piper; Andrew M. Metrailer (57) ABSTRACT

The present invention relates to a compound for use in detecting "reader" and "eraser" proteins of lysine lipoylation. The present invention provides an affinity-based probe, referred to herein as "KPlip", capable of interrogating the lipoylated peptide/protein interactions under native cellular environments. The chemical probe allows for the identification of potential regulators of lysine lipoylation, thus uncovering new biology related to lipoylation. There is also provided a method of using the compound to identifying proteins that interact with lipoylated proteins.

1 Claim, 8 Drawing Sheets

COMPOUND AND A METHOD FOR IDENTIFYING A PROTEIN USING SAID COMPOUND

CROSS-REFERENCE TO RELATED APPLICATIONS

The present application claims priority to U.S. Provisional Application No. 63/040,060 filed with the United States Patent and Trademark Office on Jun. 17, 2020 and entitled "COMPOUND AND A METHOD FOR IDENTIFYING A PROTEIN USING SAID COMPOUND," which is incorporated herein by reference in their entirety for all purposes.

The present invention relates to compounds for use in detecting "reader" and "eraser" proteins of lysine lipoylation. The present invention also pertains to a method of identifying a protein using said compounds.

BACKGROUND

Lysine lipoylation is a posttranslational modification (PTM) of a lysine residue. Lysine PTMs are highly prevalent in living organisms and play an important role in regulating diverse biological processes such as gene transcription, DNA repair, chromatin structure modulation and metabolism. Lysine lipoylation is a highly conserved lysine PTM found in a broad range of organisms ranging from bacteria to mammals. Functionally, lipoylated lysine is known to act as an essential cofactor for maintaining the activity of essential metabolic multimeric enzyme complexes, such as the pyruvate dehydrogenase (PDH) complex. Dysregulation of lysine lipoylation leads to malfunctions of metabolic complexes and numerous diseases.

Biological regulations of lysine lipoylation depend on proteins that function as the "writers", "readers" and "erasers" of lysine lipoylation. Dissecting lysine lipoylation at the proteomic level can reveal potential drug targets in the dynamic regulation of cellular metabolism. Thus, it is desirable to identify proteins that bind or remove lysine lipoylation.

In a recent article, Cristea et al. discovered that Sirt4 could interact with the PDH complex using immunoenrichment methods. The study revealed that Sirt4 is the first mammalian enzyme that can modulate PDH activity through delipoylation in living cells. However, it was noted that the delipoylation activity of Sirt4 in vitro was rather weak, especially when compared with the deacetylation activity of sirtuins. This raises an question: whether there are other enzymes that can erase lysine lipoylation more efficiently in the native cellular environment.

To this end, the present invention provides a robust chemical tool to aid in understanding the biological functions of lysine lipoylation. Specifically, the present invention provides a compound, the first affinity-based probe, referred to herein as "KPlip", capable of interrogating the lipoylated peptide/protein interactions under native cellular environments. The chemical probe allows for the identification of potential regulators of lysine lipoylation, thus uncovering new biology related to lipoylation.

Until now, no single-step fluorescent probe has been developed to report delipoylation activity. The present invention also provides a fluorogenic probe, KTlip, to detect delipoylation activity in a continuous manner. The probe enables a quick and reliable examination into whether a given protein possesses delipoylation activity.

BRIEF SUMMARY OF THE DISCLOSURE

In a first aspect of the present invention there is provided a compound comprising a formula of $R_1$—X with X being a lysine-containing peptide substituted or unsubstituted with a lipoyl group, and $R_1$ being a carbonyl having a photo-crosslinking group. The compound of the present invention may be referred to as KPlip.

Preferably, the compound is a compound of formula of $R_1$—X, wherein X is a lysine-containing peptide with at least one (preferably 1) lysine within the peptide being substituted with a lipoyl group, and $R_1$ comprises a photo-crosslinking group attached to the lysine containing peptide via a carbonyl group.

In certain embodiments the $R_1$ group is attached at the N-terminus of the lysine-containing peptide X.

In certain embodiments X comprises a peptide sequence of a protein selected from branched-chain α-ketoacid dehydrogenase (BCKDH), α-ketoglutarate dehydrogenase (KDH), pyruvate dehydrogenase (PDH), glycine cleavage complex (GCV), and histone.

In certain embodiments $R_1$ further contains an alkynyl group.

In certain embodiments X comprises a peptide sequence of a protein selected from branched-chain α-ketoacid dehydrogenase (BCKDH), α-ketoglutarate dehydrogenase (KDH), pyruvate dehydrogenase (PDH), glycine cleavage complex (GCV), or histone; and $R_1$ further contains an alkynyl group.

In certain embodiments $R_1$ is:

wherein $R_2$ is a photo-crosslinking group.

In certain embodiments, $R_2$ is a C5 straight alkyl chain substituted with diazirine, phenyl azide, ortho-hydroxyphenyl azide, meta-hydroxyphenyl azide, tetrafluorophenyl azide, ortho-nitrophenyl azide, meta-nitrophenyl azide, azido-methylcoumarin, or psoralen.

In certain embodiments the photo-crosslinking group comprises a diazirine.

In certain embodiments $R_1$ is:

In certain embodiments the compound of formula $R_1$—X has a structure according to Formula (I):

Formula (I)

with $X_1$ being the lysine-containing peptide substituted with a lipoyl group; and $R_2$ being a C5 straight alkyl chain substituted with diazirine, phenyl azide, ortho-hydroxyphenyl azide, meta-hydroxyphenyl azide, tetrafluorophenyl azide, ortho-nitrophenyl azide, meta-nitrophenyl azide, azido-methylcoumarin, or psoralen.

In certain embodiments the compound of formula $R_1$—X has a structure of Formula (II) or a structure of Formula (III):

Formula (II)

Formula (III)

wherein S, D, A, S, V and T represent amino acids using the one letter amino acid code.

Preferably, the compound of formula $R_1$—X has a structure of Formula (II).

In a second aspect of the present invention, there is provided a method for identifying a protein that binds to a lipoylated peptide, wherein the method comprises the step of adding a first compound and a second compound into a first sample, comprising a protein, to form a first mixture, wherein the first and the second compounds comprise a formula of $R_1$—X with X being a lysine-containing peptide substituted or unsubstituted with a lipoyl group, and $R_1$ being a carbonyl having a photo-crosslinking group; and wherein the first and the second compounds are different from each other.

In certain embodiments of the method the first compound comprises a lysine containing peptide substituted with a lipoyl group and the second compound comprises a lysine containing peptide unsubstituted with a lipoyl group.

Preferably, there is provided a method for identifying a protein that binds to a lipoylated peptide, wherein the method comprises the step of preparing a mixture of a first compound and a second compound with a first sample to form a first mixture, wherein the first compound has a structure of formula $R_1$—X, wherein X is a lysine-containing peptide with at least one (preferably one) lysine within the peptide being substituted with a lipoyl group, and $R_1$ comprises a photo-crosslinking group attached to the lysine containing peptide via a carbonyl group and the second compound has a structure of formula $R_1$—X, wherein X is a lysine-containing peptide, and $R_1$ comprises a photo-crosslinking group attached to the lysine containing peptide via a carbonyl group.

Optionally, the lysine containing peptide of the first compound is the same as the lysine containing compound of the second compound.

In certain embodiments of the method X of the first and second compounds comprises a peptide sequence of a protein selected from: branched-chain α-ketoacid dehydrogenase (BCKDH), α-ketoglutarate dehydrogenase (KDH), pyruvate dehydrogenase (PDH), glycine cleavage complex (GCV), and histone.

In certain embodiments of the method $R_1$ further contains an alkynyl group.

In certain embodiments of the method X of the first and second compounds comprises a peptide sequence of a protein selected from branched-chain α-ketoacid dehydrogenase (BCKDH), α-ketoglutarate dehydrogenase (KDH), pyruvate dehydrogenase (PDH), glycine cleavage complex (GCV), or histone; and $R_1$ further contains an alkynyl group; preferably the first compound is substituted with a lipoyl group while the second compound is not.

In certain embodiments the first and second compounds comprise the same peptide sequence.

In certain embodiments the first compound has a structure of Formula (II) and the second compound has a structure of Formula (III):

Formula (II)

Formula (III)

In certain embodiments the method further comprises the steps of:
- subjecting the first mixture to conditions where photo-crosslinking occurs between the protein in the first sample and the first and second compounds; and
- adding biotin azide into the first mixture, subjecting the first mixture, after the photo-crosslinking, to conditions where click reaction occurs between biotin azide and the first and second compounds; and
- conducting liquid-chromatography-mass spectrum analysis of the first mixture.

Preferably, there is provided a method for identifying a protein that binds to a lipoylated peptide, wherein the method comprises the steps of:
- preparing a mixture of a first compound and a second compound with a first sample, comprising a protein, to form a first mixture, wherein the first compound has a structure of formula $R_1$—X, wherein X is a lysine-containing peptide with at least one (preferably one) lysine within the peptide being substituted with a lipoyl group, and $R_1$ comprises a photo-cross linking group attached to the lysine containing peptide via a carbonyl group and the second compound has a structure of formula $R_1$—X, wherein X is a lysine-containing peptide, and $R_1$ comprises a photo-cross linking group attached to the lysine containing peptide via a carbonyl group;
- subjecting the first mixture to conditions where photo-crosslinking occurs between the protein and the first and second compounds;
- adding a substrate for conducting click chemistry (for example biotin azide) into the first mixture, subjecting the first mixture, after the photo-crosslinking, to conditions where click reaction occurs between biotin azide and the first and second compounds; and
- conducting liquid-chromatography-mass spectrum analysis of the first mixture.

In certain embodiments the method further comprises the steps of providing a second mixture by mixing the first compound and a third compound with a second sample, in which the second sample is from the same source of the first sample, and the first compound is substituted with a lipoyl group while the third compound comprises a lysine-containing peptide unsubstituted with a lipoyl group.

In certain embodiments the first compound has a structure of Formula (II) and the third compound has a structure of Formula (IV):

Formula (II)

Formula (IV)

In a third aspect, the present invention provides a fluorogenic probe to detect delipoylation activity in a continuous manner. The probe enables the quick and reliable examination of given proteins delipoylation activity.

In an embodiment the fluorogenic probe is a lysine-containing peptide with at least one (preferably 1) lysine within the peptide being substituted with a lipoyl group, the probe further comprising a fluorescent marker that is adapted to initiate fluorescence following de-lipoylation by undergoing an intramolecular reaction.

The fluorescent marker may be nitrobenzofurazan (NBD), for example an O-NBD. When lysine lipoylation occurs, it yields a lysine amine group. The intramolecular reaction that turns on the flourescence may be the intramolecular attack of a released amine at the O-NBD, yielding N-NBD.

In embodiments the fluorescent marker comprises one lysine amino acid and an O-NBD group. Optionally, the lysine amino acid is attached to the O-NBD group by an ether linkage. Optionally, the N-terminus of the lysine is protected, for example with a Boc group.

In embodiments the fluorescent probe has the structure of Formula (V):

Formula (V)

In accordance with a further aspect of the present invention there is provided a lysine lipoylation probe comprising a recognition group and a minimalist photo-crosslinker diazirine, wherein the recognition group is at least one peptide from different lipoylated peptides.

In certain embodiments, the different lipoylated peptides are selected from reported lipoylated proteins (for example PDH, KDH, BCKDH and GCV) and non-lipoylated proteins (e.g. histone).

The lipoylated peptides may comprise a lysine residue, particularly a lysine residue with a lipoic acid functionalized thereon.

The lipoylated peptides may also comprise an acetylated N-terminus.

In certain embodiments the different lipoylated peptides are pyruvate dehydrogenase (PDH), α-ketoglutarate dehydrogenase (KDH), α-ketoacid dehydrogenase (BCKDH), glycine cleavage complex (GCV), or histone.

In embodiments, the lysine lipoylation probe may comprise a control probe without lipoylated PTM.

In an embodiments, the lysine lipoylation probe is KPlip which contains specific lysine lipoylation posttranslational modifications (PTMs) that allows selective recognition of target proteins, and the control probe is KPlip-C which lacks PTMs. Both probes contain a minimalist photocrosslinker and an alkyne group, allowing crosslinking and proteomic profiling experiments. In addition, KPlip-comp, of which the sequence is almost the same as KPlip but without the minimalist photo-crosslinker, is used as a competing probe.

All of the probes can be utilized to perform binding and pull-down experiments in living cells and cell lysates. The experimental results indicate that the proteins bound to KPlip-C are non-specific binders. By removing those proteins from the KPlip-binding list, a probe-selectivity list is obtained. In a parallel set of binding and pull-down experiments, KPlip is utilized in the absence or presence of KPlip-comp. Any proteins that lead to a substantial (e.g. 3-fold) reduction in signal in KPlip-comp/KPlip-treated versus KPlip-treated conditions are defined as the high-specificity binder of KPlip, and by which generating a competitor-competed list. By comparing the probe-selectivity list and the competitor-competed list, a highly specific list of proteins that bind to lipoylated lysine may be obtained.

The invention may further provide a proteomic method of identifying specific mammalian proteins binding to lipoylated lysine.

The invention may further provide a kit of parts comprising a KPlip probe, a KPlip-C probe and a KPlip-comp probe.

BRIEF DESCRIPTION OF THE DRAWINGS

The invention is further described by means of example but in any limitative sense with reference to the accompanying drawings, of which.

DETAILED DESCRIPTION

Post-translational modifications (PTMs) of lysine residues are highly prevalent in living organisms and play important roles in regulating diverse biological processes such as gene transcription, DNA repair, chromatin structure modulation, and metabolism. Notable examples of lysine PTMs include methylation, acetylation, lipidation, ubiquitination, sumoylation, and others. Recently the discovery of numerous new lysine acylations, such as succinylation (Ksucc), crotonylation (Kcr), 2-hydroxyisobutyrylation (Khib), and p-hydroxybutyrylation (Kbhb), has further expanded the landscapes of lysine PTMs. Deciphering the mechanisms of these new lysine PTMs is important to further elucidate their biological functions. Research in this field has therefore seen tremendous development and attracted increasing attention in recent years.

Lysine lipoylation (Klip) is a highly conserved lysine PTM found in bacteria, viruses, and mammals. It plays a critical role in regulating cell metabolism. Klip is reported to occur on several essential metabolic multimeric complexes, including the branched-chain α-ketoacid dehydrogenase complex (BCKDH), the α-ketoglutarate dehydrogenase complex (KDH), the pyruvate dehydrogenase complex (PDH), and the glycine cleavage complex (GCV). Klip is required as an essential cofactor for maintaining the activity of these enzyme complexes. Malfunction of the lipoylated metabolic complexes, on the other hand, can lead to numerous diseases. For instance, loss of PDH lipoylation has been linked to many diseases including metabolic disorders, cancer, Alzheimer's disease, and viral infection. The enzymes that catalyze the removal of lipoylation, so called "erasers", are still poorly understood.

Using immunoenrichment methods Cristea et al. discovered that the protein Sirt4 could interact with the PDH complex. The study revealed Sirt4 as the first mammalian enzyme that can modulate PDH activity through delipoylation in living cells. However, it was noted that the delipoylation activity of Sirt4 in vitro was rather weak, especially when compared with the deacetylation activity of sirtuins. The present invention seeks to identify a probe and a method for identifying other enzymes that can erase Klip in the native cellular environment.

EXAMPLES

Example 1: Synthesis of KPlip

Profiling the interaction between an enzyme and its substrate may be difficult, as their interactions are usually weak, transient, and dynamic. Affinity-based probes (AfBPs) provide a powerful tool to overcome those hindrances by utilizing photo-crosslinking to convert transient protein-ligand interactions into covalent chemical linkages. Chemical proteomics using AfBP s coupled to mass spectrometry is a robust strategy that facilitates elucidation of complex molecular mechanisms by studying protein-ligand interactions within signaling networks.

Figure 1A:
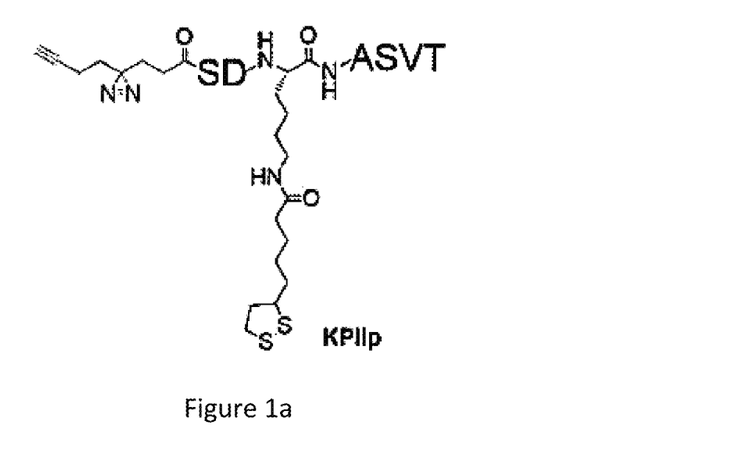
FIG. 1a is the structure of KPlip.
Figure 1B:
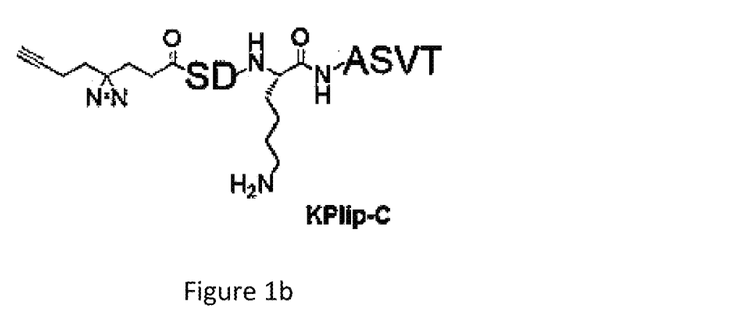
FIG. 1b is the structure of KPlip-C.
Figure 2:
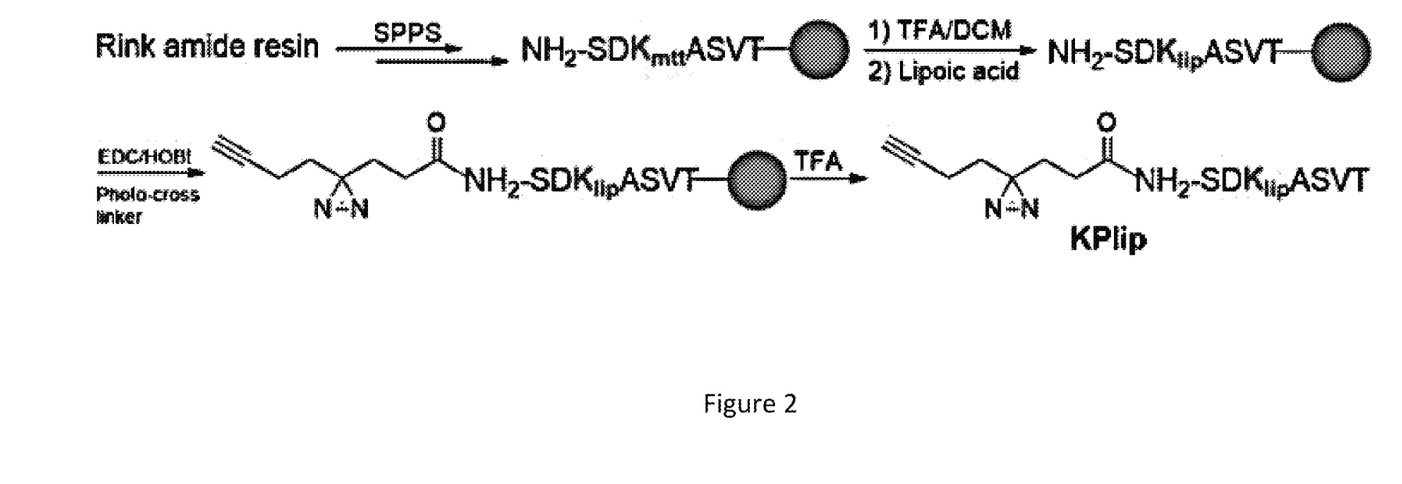
FIG. 2 shows the synthesised KPlip.

The AfBP, KPlip (FIG. 1a), was synthesised on the basis of a peptide sequence derived from BCKDH protein (K105, QSDK$_{lip}$ASVT). In the probe design, the N-terminal Gln residue was replaced by a photo-cross-linker. To synthesize KPlip, the peptide was first assembled by the standard Fmoc solid phase peptide synthesis (SPPS) method. The Mtt group in the peptide was then deprotected to allow the installation of a lipoyl group. Subsequently a photo-cross-linker with diazirine was introduced to the peptide. The synthesis is shown in FIG. 2. KPlip was further purified by HPLC and characterized by LC-MS. For comparison study, a control probe, KPlip-C, without the lipoyl moiety (FIG. 1b) was also synsthesised.

Example 2: Chemical Proteomic Profiling Using the Probe KPlip

Figure 3:
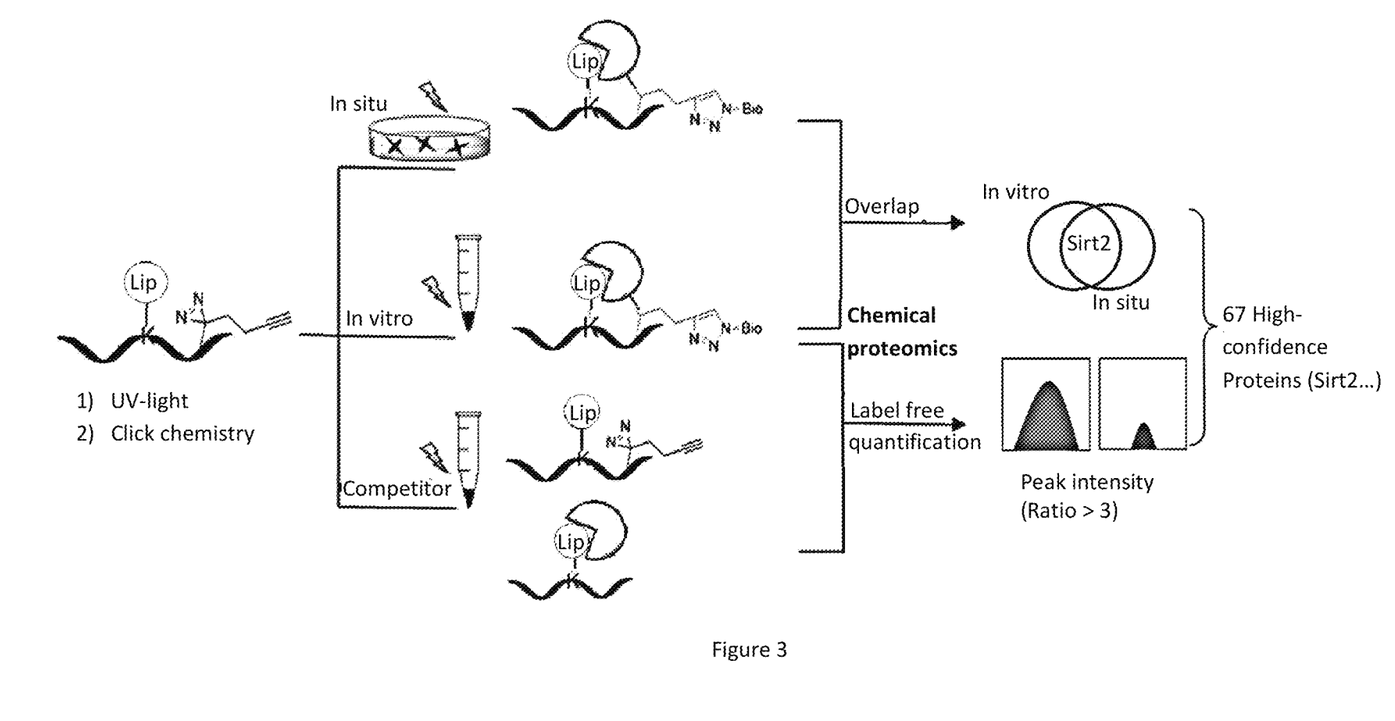
FIG. 3 shows the chemical proteomics methodology.

Using the two probes (KPlip and KPlip-C). Chemical proteomics experiments were performed. An overview of the chemical proteomics methodology is shown in FIG. 3. The chemical proteomics sought to identify potential interacting proteins of KPlip in the cellular environment. To minimize "false hits" produced by nonspecific protein binding, probe KPlip-C was used in parallel as a negative control. The probes (10 µM) were incubated with live HEK 293 cells or cell lysates for 2 h. Following ultraviolet (UV) irradiation, the KPlip/KPlip-C-labelled proteomes were clicked with biotin azide, enriched by affinity purification, resolved by SDS-PAGE, and finally analysed by LC-MS/MS. Upon removal of nonspecific binding proteins identified from the control probe KPlip-C, only the proteins that were positively identified in both lysate and live-cell experiments were chosen as potential targets. This led to a probe-selectivity list of 419 protein candidates.

Figure 1C:
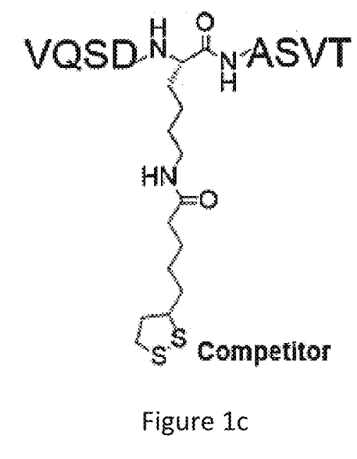
FIG. 1c is the structure of a lipoylated peptide competitor.

A series of competition experiments was performed to further identify the high-specificity binders of KPlip. HEK 293 cell lysates were preincubated with DMSO or a lipoylated peptide competitor (VQSDK$_{lip}$ASVT, FIG. 1c) at 100 µM. Subsequently the lysates were labelled with probe KPlip (10 µM) by UV irradiation. The probe-labelled proteomes were then conjugated with biotin azide, enriched by streptavidin beads, resolved by SDS-PAGE, digested with trypsin, and finally analysed by label-free LC-MS/MS quantitation. High-specificity binders of KPlip were defined as those showing substantial signal decrease (>3-fold) in the presence of the competitor. This led to a total of 588 proteins identified. The proteins identified in both the probe-selec-tivity and competition experiments were compared resulting in a high-confidence list of 67 KPlip-binding proteins.

A gene ontology (GO) analysis of the high-confidence KPlip-binding proteins was then conducted. The analysis revealed that a variety of biological processes, such as cellular lipid catabolic process and acyl-CoA metabolic process, were significantly enriched.

Sirtuin 2 (Sirt2), a member of the sirtuin family of NAD+-dependent histone deacetylase (HDAC), was identified following the analysis as a promising KPlip-binding protein.

Example 3: In-Gel Labelling of KPlip

The labelling efficiency of KPlip with recombinant Sirt2 was investigated. The Sirt2 enzyme was first incubated with either KPlip or a negative control probe, KPlip-C(lacking lipoylation), followed by 15 min of UV irradiation. Following click chemistry with rhodamine azide (Rh—N$_3$), the reaction mixtures were resolved by SDS-PAGE and analysed by in-gel fluorescence scanning. The results showed that Sirt2 was labelled by KPlip efficiently, whereas no labelling was observed in the control probe KPlip-C, indicating that Sirt2 interacted with the probe KPlip by specifically recognizing the Klip moiety. Time-dependent experiments showed that 2 min UV irradiation resulted in intense labelling. The fluorescence intensity of the labelled Sirt2 band increased when the concentrations of the probe increased, demonstrating that probe KPlip labelled the target protein in a concentration-dependent manner.

A further selectivity study was performed. This study revealed that the probe, KPlip, labelled Sirt2 more strongly than other sirtuins did, confirming that Sirt2 recognizes lipoylated lysine more preferentially than other sirtuins do. To examine whether lipoic acid of KPlip forms a disulfide bond with cysteine residues in Sirt2, excessive reducing reagent TCEP was added to the solution containing Sirt2 and KPlip prior to UV irradiation. No diminished effect of Sirt2 labelling was observed, suggesting the labelling of Sirt2 by probe KPlip was not redox-based.

Moreover, the labelling of Sirt2 can be inhibited by a lipoylated peptide competitor (VQSDK$_{lip}$ASVT, FIG. 1c), verifying that the interaction between Sirt2 and lipoylated peptide is selective and direct.

Example 4: Pull-Down Validation of KPlip

Live-cell labelling with KPlip was performed. As shown in FIG. 3, several major bands were fluorescently labelled. The control probe KPlip-C and DMSO control showed very faint or no labelling, indicating that probe KPlip recognized these proteins in a specific manner.

The physiological interaction of Klip and Sirt2 was validated using pull-down experiments. A 10 µM concentration of KPlip was incubated with live HEK 293 cells for 2 h. The treated cells were UV-irradiated and subjected to click reaction with biotin azide (Bio-N$_3$).

Figure 4:
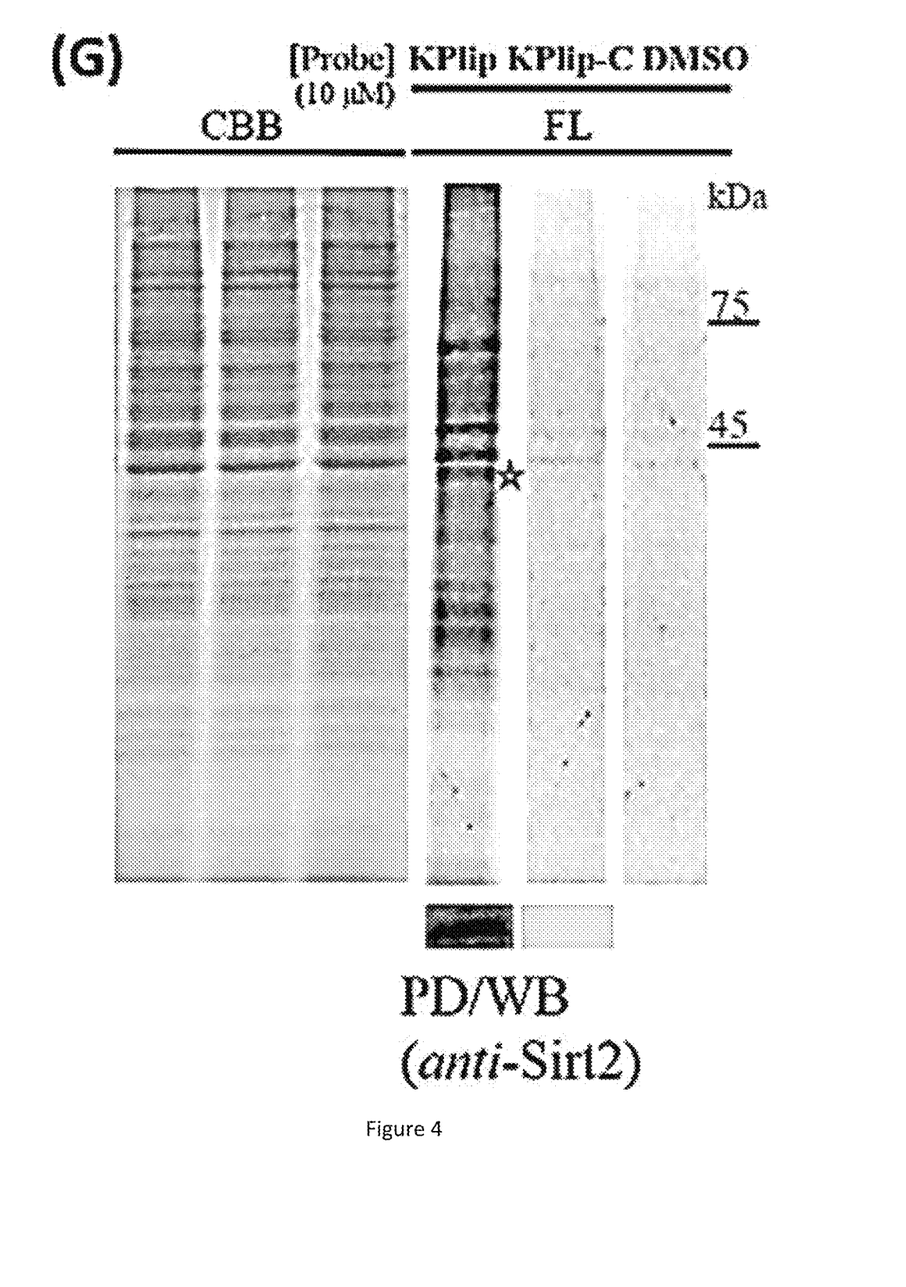
FIG. 4 shows in-gel labelling of Ive HEK293 cells with a probe of the present invention, where the Sirt2 band is labelled with an asterisk.

The cells were then lysed and enriched with streptavidin beads. The enriched proteins were finally analysed by Western blotting with anti-Sirt2. As shown in FIG. 4, Sirt2 was successfully pulled down by KPlip. In contrast, Sirt2 was not observed in the absence of probe or with the control probe (KPlip-C) (FIG. 4). These results unambiguously demonstrated that endogenous Sirt2 may be pulled down by lipoylated peptides under a native cellular environment. In addition, a pull-down assay was also performed to validate the binding of HDAC8/BRMS1L to Klip. The results showed that both proteins may be effectively pulled down by KPlip. This is consistent with the LC-MS/MS results.

These experiments confirm that KPlip is a reliable tool for chemical proteomics to dissect proteins interacting with lipoylated lysine.

Example 5: Delipoylation Study with Probe KTlip

After confirming the interactions of Sirt2 and the lipoylated peptide of the present invention in a cellular context, the capability of Sirt2 to remove a lipoyl modification was investigated. To this end, a fluorescent probe of the present invention detected delipoylation activity. Compared with mass spectrometry, radioisotopes, specific antibodies, and HPLC, fluorescent probes possess prominent advantages in detecting enzyme activity, such as high sensitivity and simple procedure. Previously, no single-step fluorescent probe has been developed to report delipoylation activity. It has been difficult to design single-step fluorescent probes for detecting deacylation activity because the aliphatic amide structure in the Kacyl group does not allow conjugation to a fluorophore.

Figure 5:
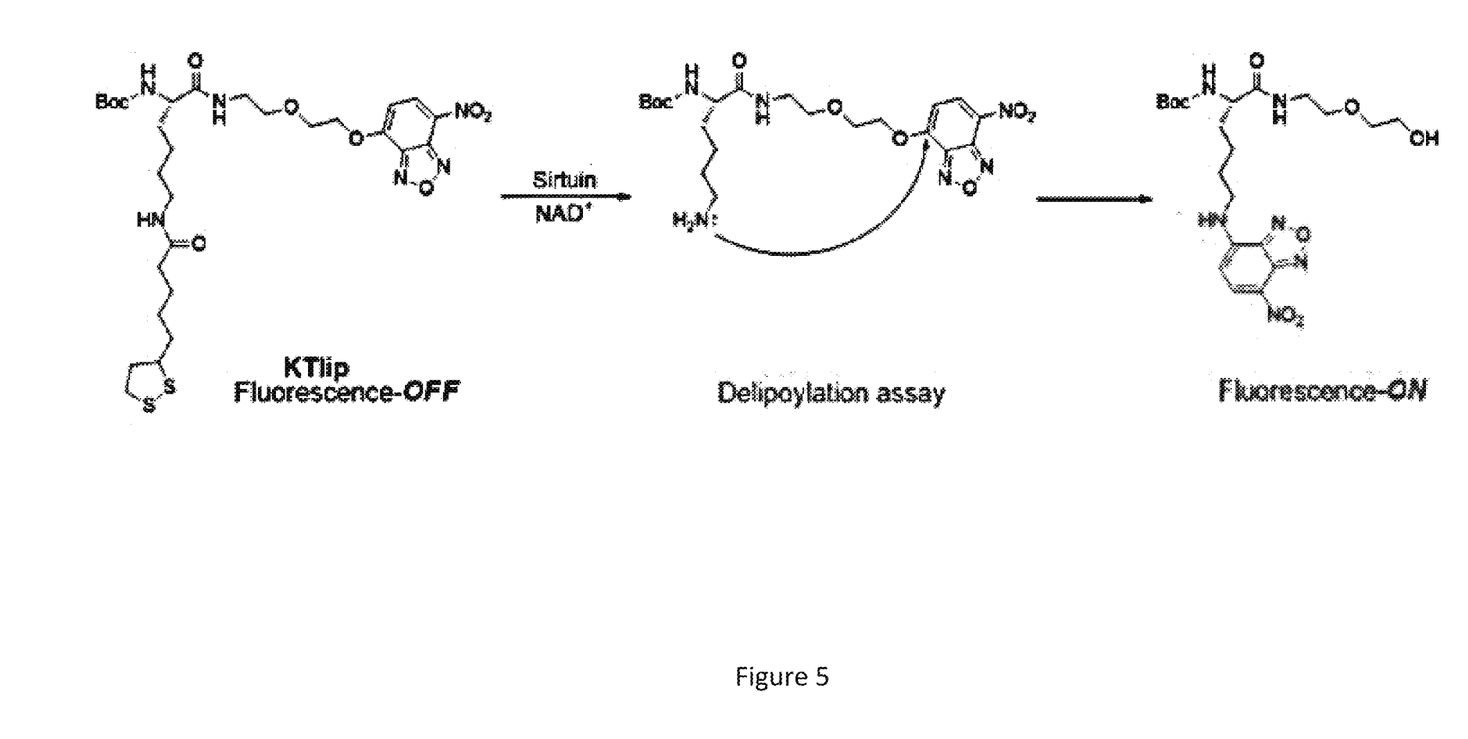
FIG. 5 shows a fluorogenic probe of the present invention KTlip along with the mechanism of fluorescence activation.

The present invention employed a fluorescent probe based on an intramolecular reaction strategy to detect deacetylation activity. As such, a fluorogenic probe, KTlip, was prepared for profiling delipoylation activity in vitro. As shown in FIG. 5, the probe consisted of a recognition group, Klip, and an O-NBD moiety. Without being bound by theory it is believed that when enzymes hydrolyze the lipoyl group, the released amine will attack the O-NBD, yielding N-NBD, and turn on the fluorescence (FIG. 5). Such a probe may report the delipoylation activity of enzymes continuously and reliably.

Figure 6:
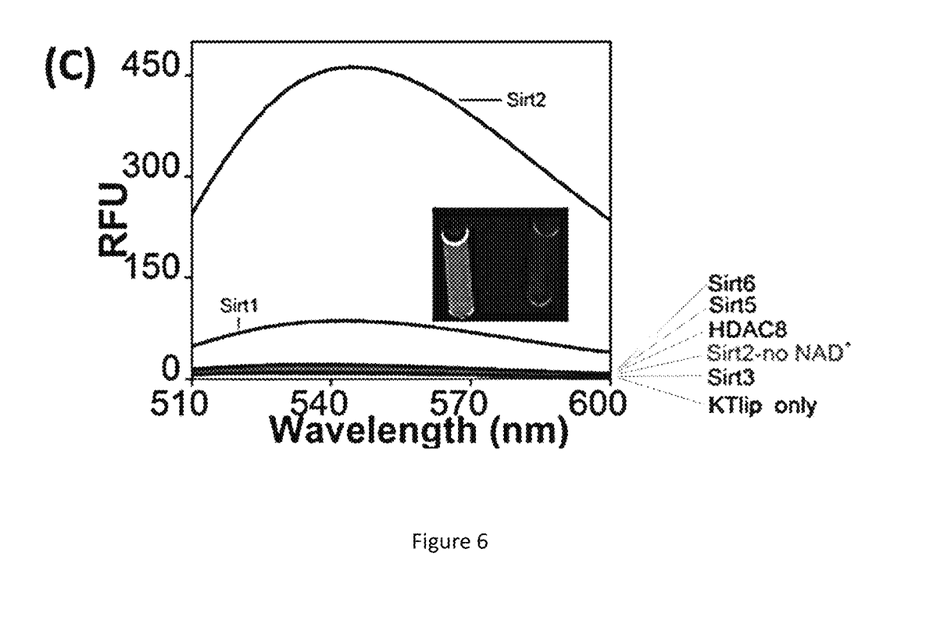
FIG. 6 shows the fluorescence measurements of a fluorescent probe of the invention against a range of proteins.

The capacity of HDACs to recognize and remove the lipoyl group of KTlip was examined by a fluorimeter assay. KTlip was incubated with various HDACs at 37° C. in HEPES buffer (pH 8.0). The fluorescence of the enzymatic reactions was then measured accordingly. As shown in FIG. 6, Sirt2 showed the strongest fluorescence increment, with 60-fold fluorescence increase. Sirt1 showed a much lower fluorescence signal, whereas Sirt3, Sirt5, Sirt6, and HDAC8 did not show a noticeable fluorescence increase. The control group without cofactor NAD+ displayed negligible fluorescence, indicating that the reaction occurred through enzymatic catalysis. Further HPLC and MS analysis confirmed that the molecular weight of the newly generated peak corresponded to the expected tandem de-lipoylated/exchanged product. No de-lipoylated product was observed under the enzymatic reaction conditions for HDAC8. After enzymatic reaction with Sirt2, a shift of peak absorption from 380 nm to 480 nm was clearly observed. Through detailed kinetic study, the first-order rate constant of the reaction was determined to be 0.013 min-1. The Km value of KTlip obtained from the fluorescent method matched well with that from the traditional HPLC method, underscoring that probe KTlip can serve as a useful tool for detecting enzymatic delipoylation activity. These data revealed that Sirt2 displays robust activity to remove the lipoyl group in vitro.

Example 6—Delipoylation Study with Various Lipoylated Peptides

An experiment was carried out to investigate whether sirtuins exhibit substrate specificity in recognizing different peptide sequences. A total of 11 lipoylated peptides (KAlip-1 to KAlip-11) were synthesised. The peptide sequences were selected from proteins that have been reported as being lipoylated (PDH, KDH, BCKDH, and GCV) and non-lipoylated proteins (e.g., histone). The peptides were synthesized with a standard Fmoc solid phase synthesis approach and characterized by LC-MS. The delipoylation activity was then determined by an HPLC assay. Sirt2 catalysed the removal of the lipoyl group for all the peptides tested, as shown in Table 1. Compared with non-putative peptides, putative lipoylated peptides appeared to be more efficiently hydrolyzed by Sirt2. For example, the delipoylated product of KAlip-1 (derived from histone) after 40 min was determined to be 59%, which is less than that of putative lipoylated substrates such as KAlip-5 and KAlip-6 (derived from PDH). Near absolute delipoylation was observed for KAlip-5 and KAlip-8 within just 15 min, signifying that Sirt2 catalyzed the removal of the lipoyl group with high efficiency.

TABLE 1

Delipoylation Study of Sirt2 with Various Lipoylated Peptide

| Peptide | Protein/Lysine | Peptide sequence | Delipoylation product$^a$ | kcat (s · 1) | Km (μM) | kcat/Km (s · 1 M · 1) |
|---|---|---|---|---|---|---|
| KAlip-1 | Histone, H3K9 | KQTARK(lip)STGGWW | 59% | 0.01 ± 0.0003 | 9.7 ± 0.2 | $1.06 \times 10^3$ |
| KAlip-2 | Dps, K10 | VKSK(lip)ATNL WW | 97% | | | |
| KAlip-3 | Pyruvate kinase, K105 | SDPIIK(lip)GSGTWW | 98% | | | |
| KAlip-4 | GDH, K503 | SGASEK(lip)DIVHSGWW | 100% | | | |
| KAlip-5 | PDH, E2, K259 | EIETDK(lip)ATIGWW | 100% | 0.061 ± 0.002 | 18.9 ± 0.6 | $3.26 \times 10^3$ |
| KAlip-6 | PDH, E3, K97 | EIETDK(lip)AVVTWW | 100% | | | |
| KAlip-7 | KDH, E2, KHO | EIETDK(lip) TSVQWW | 65% | | | |
| KAlip-8 | BCKDH, E2, K105 | VQSD K(lip)ASVTWW | 100% | 0.045 ± 0.0002 | 26.2 ± 3.3 | $1.72 \times 10^3$ |
| KAlip-9 | TNF-α, K20 | EALPKK(lip) TGGPWW | 100% | | | |
| KAllp-10 | Glycine cleavage system, K107 | ALESVK(lip)AASEWW | 71% | | | |

TABLE 1-continued

Delipoylation Study of Sirt2 with Various Lipoylated Peptide

| Peptide | Protein/Lysine | Peptide sequence | Delipoylation product[a] | kcat (s·1) | Km (μM) | kcat/Km (s·1 M·1) |
|---|---|---|---|---|---|---|
| KAlip-11 | Biotin carboxyl carrier protein, K122 | VEAMK(lip)LMNE WW | 94% | 0.023 ± 0.0002 | 13.5 ± 1.4 | $1.67 \times 10^3$ |

[a]HPLC yield of delipoylated product was monitored at 280 run after 40 min.;
— indicates data were undetermined."

Control experiments without the addition of NAD+ and enzyme unambiguously proved that the hydrolysis reaction is attributed to enzymatic activities rather than other environmental factors. In addition, the newly generated peak of KAlip-1 with Sirt2 showed the same retention time as the unmodified peptide (FIG. 3F). The delipoylation activity of HDAC8 was further examined using KAlip-5 and KAlip-1. No delipoylated product was observed. The enzymatic delipoylation results by fluorescent probe KTlip and lipoylated peptides KAlip-5 and KAlip-1 together indicated that HDAC8 has no delipoylation activity. A more detailed assessment of the enzymatic delipoylation reaction was performed. Time-dependent experiments and steady-state kinetics studies were conducted of KAlip-1, 5, 8, and 10 with Sirt2 (Table 1). Kinetics data (Table 1) revealed that the catalytic efficiency ($K_{cat}/K_m$) for delipoylation activity of Sirt2 is of the same order of magnitude as that of the deacetylation of Sirt1-2, the desuccinylation/demalonylation of Sirt5, and the demyristoylation of Sirt6 in vitro. The catalytic efficiency of Sirt2 toward the putative lipoylated peptides (KAlip-5, 8, 10) was slightly higher than toward the nonputative H3K9 lipoyl peptide (KAlip-1). Strikingly, the catalytic efficiency of Sirt2 ($K_{cat}/K_m$) to delipoylate DLAT K259 of the PDH complex (KAlip-5) is approximately 426-fold higher than that of Sirt4.

Taken together, these in vitro enzymology data demonstrated that Sirt2 is a robust delipoylating enzyme.

Example 7—Sirt2 Removes Klip from Lipoylated DLAT Protein

An experiment was performed to test whether Sirt2 delipoylates protein substrates. Recombinant DLAT protein from mammalian cells was used for a delipoylation assay. The Klip modification in DLAT was first confirmed using Western blot with a lipoic acid antibody (FIG. 3G). Subsequently DLAT was incubated with Sirt2 in the presence of cofactor NAD+, and the lipoylation level of DLAT was examined by Western blot. Negative controls with no NAD+ or no Sirt2 were included as well. Comparing with the control groups, a substantial reduction was observed in the Klip level for DLAT treated with Sirt2 in the presence of NAD+.

These results indicated that Sirt2 has delipoylation activity toward DLAT protein.

Example 8—Sirt2 Delipoylation of PDH in Living Cells

Figure 7:
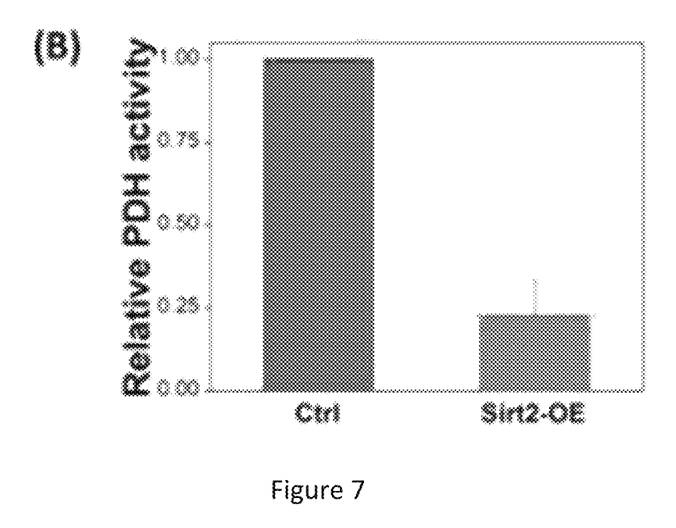
FIG. 7 shows the relative levels of PDH activity in cells overexpressing Sirt2 compared to wild-type cells

An experiment was performed to determine whether Sirt2 could delipoylate the physiological substrate in living cells. Lipoylated PDH is responsible for converting pyruvate into acetyl-CoA, a central metabolite that enters into the TCA cycle. On the other hand, the delipoylation of PDH impairs its activity. Although the cellular localization of Sirt2 was conventionally annotated to be in the cytosol/nucleus, recent literature has suggested that Sirt2 could localize to mitochondria and regulate the functions of mitochondrial proteins. Sirt2 was detected in a mitochondrial fraction isolated from HeLa S3 cells overexpressing Sirt2. It was investigated whether Sirt2 can delipoylate PDH and regulate its function in living cells. Sirt2 was overexpressed in HeLa S3 cells by transfecting cells with pCMV4a-Sirt2 vector. After transfection, the cells were harvested and lysed. Western blot experiments confirmed effective Sirt2 overexpression. The obtained cell lysates were then subjected to a PDH activity assay. As shown in FIG. 7, PDH activity in cells overexpressing Sirt2 was significantly decreased compared to that in wild-type cells. The lipoylation level of DLAT (E2 subunit of PDH) was decreased in cells overexpressing Sirt2, whereas the total level of DLAT remained unchanged. Furthermore, siRNA knock-down experiments were performed to examine the regulatory effect of endogenous Sirt2 on the lipoylation of PDH. Effective siRNA-mediated knockdown of Sirt2 was confirmed. Notably, Sirt2 knockdown led to an elevated lipoylation level in DLA. Concomitantly, increased PDH activity was also observed. These results demonstrated that Sirt2 can effectively catalyse DLAT delipoylation and modulate PDH activity in cells The present invention provides a panel of chemical probes to investigate the regulatory mechanism of lysine lipoylation. The developed AfBP probe KPlip is capable of capturing Klip-interacting proteins in both living cells and cell lysates. Chemical proteomics experiments with KPlip identified Sirt2 as a novel binder of a lipoylated substrate. KTlip is the first single-step fluorescent probe developed for rapid profiling of delipoylation activity. The enzymology data obtained from both KTlip and lipoylated peptides demonstrated the robust delipoylation ability of Sirt2 in vitro. The delipoylation activity of Sirt2 is far superior to that of Sirt4, the only identified mammalian delipoylating enzyme.

With the chemical probes of the present invention the novel function of Sirt2 has been proven to remove the lipoyl group with high catalytic efficiency. Furthermore, it was also shown that Sirt2 could effectively catalyze DLAT delipoylation and downregulate PDH activity in cells. This suggested that sirtuins might play a complex role in the dynamic regulation of PDH activity through different deacylation mechanisms. The probes of the present invention provide useful tools to further advance the understanding of lipoylation and other acylation in biology and diseases.

General Information.

Sirtuins, including Sirt1, Sirt2, Sirt3, SirtS, and Sirt6, were recombinantly expressed and purified. Pyruvate dehydrogenase E2 (DLAT) (NM_001931) human recombinant protein was sourced from ORIGENE. Streptavidin magnetic beads were purchased from New England Biolabs. In-gel fluorescence scanning experiments were performed with a FLA-9000 Fujifilm scanner. Antibody of Sirt2 (D4S6J) was from Cell Signaling. Antibodies of DLAT (abl72617), lipoic acid (ab58724), HDAC8 (abl87139), BRMSIL (ab107171), and Hsp60 (abl28567) were from Abcam. IRDye 680RD donkey anti-rabbit IgG (secondary antibody) was purchased from LI-COR Biosciences. Immobilon-FL poly(vinylidene difluoride) membrane for Western blotting was purchased from Merck Millipore. Western blotting was carried out with a C600 Azure biosystem. Sirt2 siRNA (AM16708) was from ThermoFisher Scientific. The plasmid pCMV4a-SIRT2-Flag was purchased from Addgene (plasmid #102623).20 The sequencing grade modified trypsin was purchased from Promega.

Cu(I)-Catalyzed Cycloaddition/Click Chemistry.

20 μM azide reagent was added to the protein samples labelled by KPlip and KPlip-C. Tris(2-carboxyethyl)phosphine (0.4 mM), tris(3-hydroxypropyltriazolylmethyl)amine (40 μM), and CuSO 4 (0.4 mM) were then added. The reaction was kept at room temperature for 2 h.

Affinity Enrichment of Biotinylated Proteins.

After click chemistry reaction of KPlip or KPlip-C using biotin-azide (Bio-$N_3$), chilled acetone was added to precipitate the proteins. The pellets were then washed with cold methanol and air-dried. The obtained pellets were redissolved in PBS buffer containing less than 0.5% sodium dodecyl sulfate (SDS) by heating and vortexing. Streptavidin magnetic beads were then added and shaken gently at room temperature for 4 h. The beads were collected by a magnet and washed with 0.1% SDS/PBS once and PBS twice. The beads were redissolved in 1×SDS loading buffer, and proteins were released/denatured by boiling at 95° C. for 20 min.

In-Gel Digestion by Trypsin.

The pull-down sample was separated on 12% SOS-PAGE gel and stained with the Ruby protein staining method. The gel was cut into pieces. The collected gel was washed by 100 mM ammonium bicarbonate buffer, reduced by DTT (5 mM) at 50-60° C. for 30 min, alkylated by iodoacetamide (25 mM) at room temperature for 45 min, dehydrated by 95% ethanol, and digested by sequencing grade modified trypsin at 37° C. overnight. After that, the digested solution was collected. The gel was further extracted twice using 50% acetonitrile containing 5% formic acid. The combined solution was dried by speed vacuum for LC-MS/MS analysis.

LC-MS/MS Analysis.

Upon extraction from the gel and desalting, the obtained peptides were redissolved in 12 μL of 0.1% formic acid and separated by an Easy-nLC 1200 system coupled to a QExactive HF (Thermo Scientific). A 5 μL amount of peptide was injected and separated on a reverse phase C18 column (75 μm×15 cm) at a flow rate of 250 nL/min. Mobile phase A (0.1% formic acid in ultrapure water) and mobile phase B (0.1% formic acid and 80% acetonitrile in ultrapure water) were used to establish a linear gradient of 7-25% mobile phase B in 50 min. Peptides were then ionized by electrospray at 1.5 kV. The mass spectrometer was operated in positive ion mode at a resolution of 120 000, with a full MS spectrum (m/z=350-1800) using an automatic gain control (AGC) target of $3\times10^6$. Higher-energy collisional dissociation (HCD) fragmentation was conducted with the 12 most intense ions (normalized collision energy 27). MS/MS spectra were acquired with an AGC target of $1\times10^5$ at a resolution of 30 000. The dynamic exclusion time was set to 30 s.

Proteomics Analysis.

The raw data were created by XCalibur 4.0.27 (Thermo Scientific) software and processed with Proteome Discoverer (PD) software suite 2.2 (Thermo Scientific), against UniProt human protein database (downloaded on 20171010) in Sequest HT node. The precursor and fragment mass tolerances were set to 10 ppm and 0.02 Da, respectively. Reversed database searches were used to evaluate false discovery rate (FDR) of protein and peptide identifications. A maximum of two missed cleavage sites of trypsin was allowed. Carbamidomethylation (C) was set as static modification, and oxidation (M) and acetyl (N-terminus) were set as variable modifications. FDR of peptide spectrum matches and peptide identification were determined using the Percolator algorithm at 1% based on q-value. The abundance values of proteins were obtained via a label-free quantification method using Proteome Discoverer 2.2. Minora feature alignment and feature mapping were applied to calculate the abundance of peptides in the MS1 scan. Lists of protein identifications and quantification are attached in Supplementary Data 2.

Bioinformatic Analysis.

For protein functional associations and protein-protein interaction analysis. Web-based analytic tools were used. Gene ontology analysis was performed in Metascape 3.0 (http://metascape.org) to explore GO terms and enrichment analysis of target proteins. Terms with a p-value <0.01, a minimum count of 3, and enrichment factor >1.5 (the enrichment factor is the ratio between the observed counts and the counts expected by chance) were set as the cut off criteria. Subsequently, the protein interaction biological networks of identified proteins were constructed based on the STRING 11.0 database (http://www.string-db.org) under the standard settings. In addition, the network data was exported to simple tabular text. The text was used to build protein interaction networks, which were then visualized and evaluated in Cytoscape software (v.3.7.1).

In-Gel Fluorescence Scanning.

After click chemistry reaction with rhodamine-azide, chilled acetone was added to the reaction mixtures. The reaction was then placed in a −20° C. freezer for 1 h to precipitate the proteins. The pellets were washed with cold methanol and air-dried. Finally, they were redissolved in 1×SDS loading buffer by heating at 95° C. for 10 min and then resolved by SDS-PAGE. The labelled proteins were visualized using a FLA-9000 Fujifilm scanner (Ex=532 nm).

Western Blotting.

To perform Western blotting experiments, samples were first separated by SDS-PAGE and then transferred to an Immobilon-FL polyvinylidene difluoride (PVDF) membrane. The samples were blocked with 5% nonfat milk in TBST (0.1% Tween in Tris-buffered saline) at room temperature for 1.5 h. Subsequently the membrane was incubated with primary antibody (anti-sirt2/antilipoic acid/anti-DLAT) at 4° C. overnight. After incubation, the membrane was washed with TBST (3×5 min) gently at room temperature. Following that, the membrane was incubated with the secondary antibody (IRDye 680RD donkey anti-rabbit IgG) at room temperature for another 1 h. It was then washed with TBST (3×5 min). Finally, the membrane was applied to fluorescence scanning.

Absorption and Fluorescence Study of Probe KTlip.

The probe KTlip was incubated with sirtuin and NAD+ at 37° C. in 20 mM HEPES buffer (pH 8.0) containing 150 mM NaCl, 1 mM $MgCl_2$, and 2.7 mM KCl. The enzymatic reaction volume was 50 μL. When the enzymatic reaction was complete, the reaction was applied for absorption and fluorescence measurement. The parameter set for absorbance measurement was as follows: UV-visible light, collection region: 300-550 nm. The parameter set for fluorescence measurements was as follows: $\lambda_{ex}$=480 nm, slit width: 5 nm, collection region: 510-600 nm.

Determination of the First-Order Rate Constant k.

The rate constant was calculated by fitting the fluorescence data to the following equation:

Fluorescence intensity=1−exp(−$kt$)

Enzymatic Reaction with Lipoylated Peptides.

The lipoylated peptides KAlip-1 to -11 were incubated with sirtuin and cofactor NAD+ at 37° C. in 20 mM HEPES buffer (pH 8.0) containing 150 mM NaCl, 1 mM MgCl$_2$, and 2.7 mM KCl. The reaction volume was set to 50 μL. At each specific reaction time point, the reaction mixtures were quenched by adding 250 μL of methanol. The reactions were vortexed and centrifuged. Supernatant was collected and then analysed by reverse phase HPLC. The new peak generated was collected for ESI-MS or MALDI-TOF-MS analysis directly.

Kinetic Study with Lipoylated Peptides.

To determine the values of $k_{cat}$, and $K_m$, purified Sirt2 with 400 μM NAD+ was incubated with different concentrations of lipoylated peptide (0-120 μM) in 20 mM HEPES buffer (pH 8.0) containing 150 mM NaCl, 1 mM MgCl$_2$, and 2.7 mM KCl at 37° C. for 10 min (KAlip-1 and KAlip-10) or 5 min (KAlip-5 and KAlip-8). The reactions were quenched by adding 250 μL of methanol and then applied for HPLC analysis with a linear gradient of 5% to 85% B (acetonitrile) for 30 min. The generated delipoylated product was quantified based on the peak area monitored at 280 nm. The $k_{cat}$, and $K_m$, values were calculated by curve-fitting $V_{initial}$/[E] versus [S]. The experiments were conducted in duplicate.

PDH Activity Assay.

To overexpress Sirt2 in cells, pCMV4aSirt2Flag vector was transfected into HeLa-S3 cells using Lipofectamine 2000 (Invitrogen). The activity of PDH was assessed by measuring absorbance at 450 nm using a microplate assay kit (pyruvate dehydrogenase enzyme activity microplate assay, Abcam, ab109902). A 1000 μg amount of cell protein extracts was used for PDH immunocapture in each well. The experiments were performed in duplicate.

Mitochondria Isolation.

The mitochondrial fraction was isolated according to the manufacturer's instructions using a mitochondria isolation kit (Thermo Fisher, cat. No. 89874). The experiments were performed in duplicate.

The invention claimed is:

1. A method for identifying a protein that binds to a lipoylated peptide comprising the steps of:
   (a) forming a first mixture by adding a portion of a first compound and a second compound into a portion of a sample containing the protein, and forming a second mixture by adding a remaining portion of the first compound and a third compound into a remaining portion of the sample containing the protein, wherein, the first compound has a structure of Formula (II), the second compound has a structure of Formula (III) and the third compound has a structure of Formula (IV):

(b) subjecting the first mixture of step (a) to conditions where photo-crosslinking occurs between the protein and the first compound or the second compound of the first mixture;
   (c) adding biotin azide into the product of step (b);
   (d) subjecting the product of step (c) to conditions where click reaction occurs between biotin azide and the first compound or the second compound;

(e) subjecting the product of step (d) to affinity purification, SDS-PAGE and liquid chromatography mass spectrum (LC-MS) analysis to remove non-specific protein binding to the second compound, while producing a first LC-MS intensity of the protein that binds to the first compound;

(f) subjecting the second mixture of step (a) to conditions where photo-crosslinking occurs between the protein and the first compound of the second mixture;

(g) adding biotin azide into the product of step (f);

(h) subjecting the product of step (g) to conditions where click reaction occurs between biotin azide and the first compound;

(i) subjecting the product of step (h) to affinity purification, SDS-PAGE and LC-MS analysis to produce a second LC-MS intensity of the protein that binds to the first compound; and (j) determining whether the first LC-MS intensity of step (e) is at least 3-fold higher than the second LC-MS intensity of step (i) in order to identify whether the protein binds to a lipoylated peptide.

\* \* \* \* \*